United States Patent [19]
Korth

[11] Patent Number: 5,885,277
[45] Date of Patent: Mar. 23, 1999

[54] HIGH-FREQUENCY SURGICAL INSTRUMENT FOR MINIMALLY INVASIVE SURGERY

[75] Inventor: Knut Korth, Merzhausen, Germany

[73] Assignee: Olympus Winter & Ibe GmbH, Hamburg, Germany

[21] Appl. No.: 765,642
[22] PCT Filed: Jul. 1, 1995
[86] PCT No.: PCT/EP95/02554
  § 371 Date: Feb. 27, 1997
  § 102(e) Date: Feb. 27, 1997
[87] PCT Pub. No.: WO96/02196
  PCT Pub. Date: Feb. 1, 1996

[30] Foreign Application Priority Data

Jul. 15, 1994 [DE] Germany .......................... 44 25 015.0

[51] Int. Cl.⁶ .................................................. A61B 17/36
[52] U.S. Cl. .................................. 606/35; 606/41; 606/46
[58] Field of Search .......................... 606/32–52; 604/20, 604/27

[56] References Cited

U.S. PATENT DOCUMENTS 4,030,502 6/1977 Iglesias ...................................... 606/46
4,936,301 6/1990 Rexroth et al. ........................... 606/45

*Primary Examiner*—David M. Shay
*Attorney, Agent, or Firm*—Walter C. Farley

[57] ABSTRACT

The invention concerns an endoscopic instrument for the high frequency surgical treatment of tissue in body cavities by using a liquid produced as a result of a wash penetrating the cavity. The instrument has a shaft which can be introduced into the cavity and by means of which an active electrode can be placed in the liquid volume. The instrument further has a neutral electrode and a high-frequency generator to which both electrodes are connected by insulated leads. The invention is characterized in that the neutral electrode is arranged at a distance from the active electrode in the liquid volume.

4 Claims, 1 Drawing Sheet

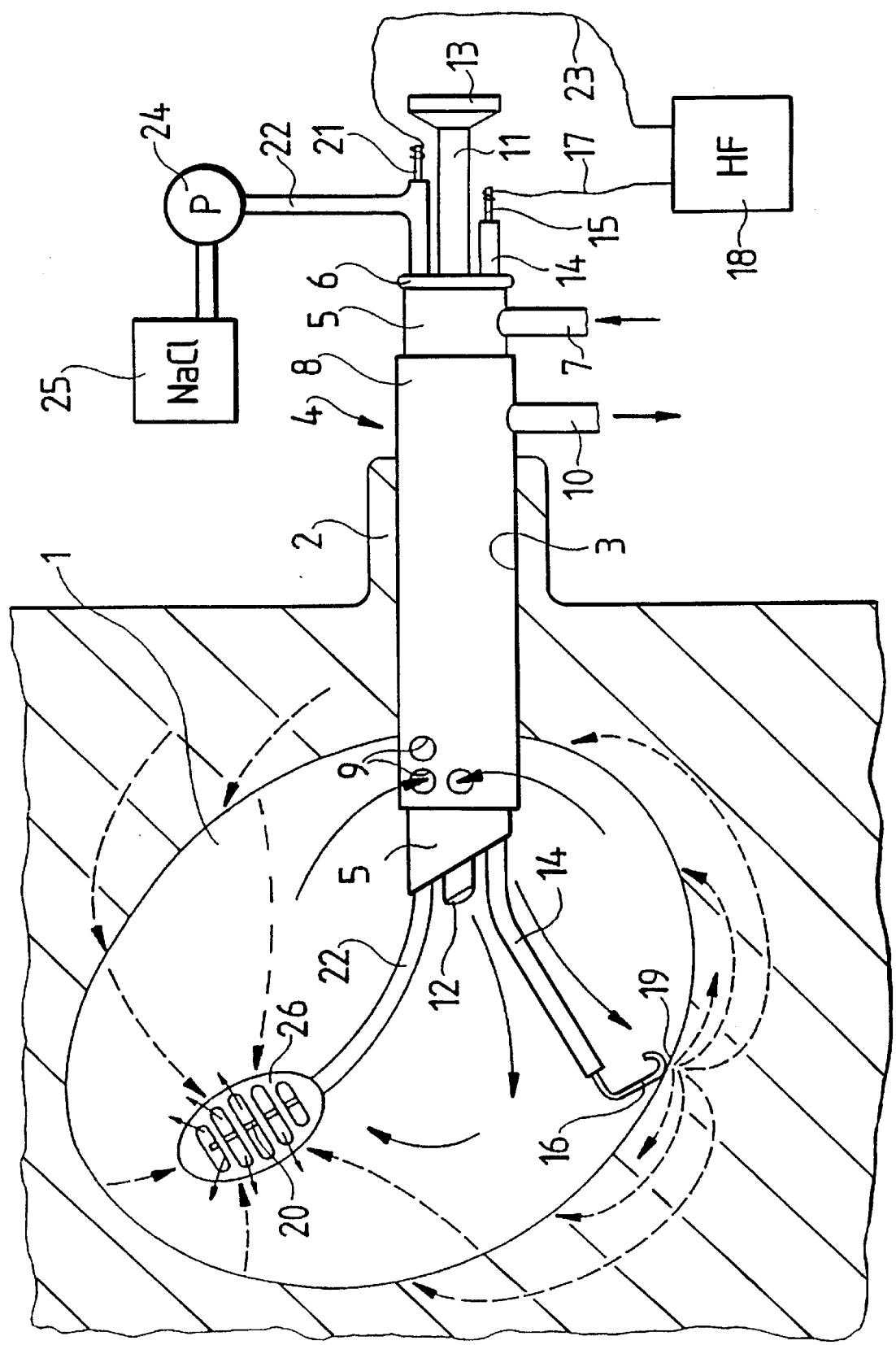

HIGH-FREQUENCY SURGICAL INSTRUMENT FOR MINIMALLY INVASIVE SURGERY

This invention relates to endoscopic instruments of the species defined in the preamble of claim 1.

Such instruments allow surgery in arbitrary liquid-filled cavities such as the uterus or the intestine. Depending on the selected electrode and adjustment of the hf power, incisions may be made or bleeding be stopped by surface coagulation. Such instruments are used particularly in urology to operate on the bladder wall and especially for prostate resection.

The active electrode designed for cutting or for coagulation initially is placed in the liquid body or volume. Even if the hf generator is already turned on, current will not yet flow because the rinsing liquid is lean in electrolyte and is a poor electrical conductor. Current starts flowing when contact is made with the tissue which is rich in electrolyte and is a good conductor. The current then flows through the tissue to the neutral electrode.

In known instruments of the initially cited kind, the neutral electrode is mounted spaced from the body cavity, namely always on the body surface. In urological surgery, the neutral electrode frequently is wound around the thigh and on the skin.

This procedure has the drawback of a long and hence high-resistance current path through the body from the contact site of the active electrode with the tissue to the distant body surface zone in contact with the neutral electrode. There is danger of so-called stray currents which may lead to skin burns, for instance if the patient makes contact with a metallic object such as the operating table. Such stray currents lead to problems if the patient is making simultaneous contact with other metal conductors such as EKG electrodes and the like. Moreover, and in an exceedingly undesirable manner, the hf current also can jump through the endoscope optics toward the surgeon's eye. Many problems arise when the neutral electrode is poorly affixed. If such a neutral electrode makes contact only by a small area with the body surface, burns again are incurred.

Furthermore, the large penetration depth in the tissue underneath the active electrode is also a drawback. When the neutral electrode is connected to the body surface, the current flows from the contact site of the active electrode into the depths of the tissue and may still inflict thermal injury to the tissue far below those tissue layers where cutting is intended. As a result, undesired and very deep thermal injury is sustained, requiring long healing times and injuries which are susceptible to infection.

A so-called bipolar electrode system is known, wherein the neutral electrode is mounted in the vicinity of the active electrode and in contact with the body surface. The purpose of this configuration is to make the current between the two electrodes flow through the tissue along the shortest path. Illustratively, such an instrument is disclosed in German patent document 25 21 719 C2. However, it suffers from the drawback of design-entailed small contact area between body tissue and neutral electrode, causing high current density in the tissue.

An object of the present invention is to create instruments of the initially cited kind allowing elimination of the above cited drawbacks and hence permitting more reliable work with respect to the incision depth of influence and providing general electrical safety.

This problem is solved by the invention by the features of the characterizing part of claim 1.

In the invention, the neutral electrode is mounted a distance from the active electrode inside the same liquid volume and thereby also in the body cavity. Accordingly, current can only flow in the narrower zone of the body cavity. All safety problems raised by stray currents are thereby automatically eliminated. Moreover, the current's depth effect is substantially less when cutting or coagulating: the current does not flow depth-wise from the contact site between the active electrode and the tissue but preferentially sideways to spread in the body tissue—which is more conducting than the liquid volume—laterally on the surface of the body cavity and to pass from said cavity into said liquid volume and flow at low current density to the neutral electrode. As a result, there is high current density at the active electrode as required for cutting or coagulation. But in the other surface zones of the body cavity, the current returns at low surface density, that is without cutting, into the liquid volume. Safety relating to depth effects during cutting is considerably heightened thereby. Burning sensitive tissue parts below the surgically treated tissue layer is avoided.

The features of claim 2 are advantageous. Unavoidably, the liquid volume always contains some portion of electrolyte and hence evinces raised conductivity. This phenomenon is caused in part by inevitable inflows of urine or blood, increasing the electrolyte content. Moreover, this conductivity is desirable for the low-resistance and large-area return of the current through the surface of the liquid volume to the neutral electrode. The liquid volume also may be enriched as a whole with electrolyte, for instance by adding electrolyte to the rinsing liquid which ordinarily is constantly fed into the liquid volume during electro-surgery. Good conductivity between the neutral electrode to the adjoining body surfaces is achieved by enriching the liquid volume with electrolyte. On the other hand, however, the good conductivity of the liquid volume also causes a current directly through the liquid volume between the active and neutral electrodes. Although this direct-path current between the electrodes does not stress the tissue of the patient and therefore is medically unobjectionable, still this direct-path current loads the high-frequency power source feeding the current and may be disadvantageous in this respect. It may be preferable therefore, as stated by the features of claim 2, that there shall be a liquid low in electrolyte in the vicinity of the active electrode to avert a direct-path current between the active and the neutral electrodes. In such a case current will flow only into the body tissue when the active electrode touches the body tissue and from there through the body tissue to the body surface zones which adjoin zones of the liquid volume fairly substantially enriched with electrolyte where the liquid volume is more conductive and thereby assures current contact with the neutral electrode.

The features of claim 3 are also advantageous. These features assure that the liquid volume be kept rich in electrolyte outside the region of surgery, that is, that it be kept good-conducting. Preferably and simultaneously, rinsing liquid free of electrolyte is supplied to the treatment zone of the active electrode and liquid rich in electrolyte is supplied to the regions outside this zone. Electrolyte enrichment is implemented advantageously as defined in claim 4 in the immediate vicinity enclosing the neutral electrode in order to improve current flow at said electrode. In this manner very small neutral electrodes may be used.

The features of claim 5 are advantageous. Thereby, with permanent evacuation of liquid and simultaneous feed of electrolyte-lean liquid and of electrolyte-rich liquid, a constant equilibrium can be achieved, there being an electrolyte gradient from the treatment zone of the active electrode to the peripheral zone of the neutral electrode.

The features of claim 6 are advantageous. All said devices and also the neutral electrode may be placed in mutually separate manner with several insertion tubes into the cavity. As regards urological work in the bladder, a suprapubic puncture technique for instance is appropriate, comprising an access through the urethra to the bladder and another access through a supra-pubically placed tube. Illustratively, the neutral electrode may be put in place through the supra-pubic tube. The liquid inlet device may be one of the tubes and the liquid evacuation device may be the other tube. The features of claim 6 are advantageous, whereby the neutral electrode and all cited rinsing and evacuation devices are mounted alone or severally in the tube. Preferably, all cited devices are mounted in that tube which in urology usually serves as the continuous flow shaft or tube with feed and evacuation lines, both electrodes being put in place through said permanent tube which also comprises an electrolyte feed to the neutral electrode zone.

The features of claim 7 are advantageous. In this manner the neutral electrode is enclosed by a contact-guard preventing this neutral electrode from coming into contact with tissue entailing undesired burns.

The invention is shown in illustrative manner and in schematic section through a body cavity with an endoscope inserted therein.

The single FIGURE shows in highly diagrammatic manner and in section a body part of a male patient with bladder 1, penis 2, and urethra 3 with inserted endoscope 4.

An endoscope 4, shown in highly diagrammatic manner, is mounted with its distal end in the bladder 1, passing through the urethra 3 and terminating at its proximal end into the surroundings. Endoscope 4 comprises a tube 5 open at the distal end and fitted at its proximal end with a closure means 6 not elucidated further which, in the diagrammatic embodiment shown by example, may be a membrane sealing element.

Rinsing liquid is introduced in the direction of the shown arrow into a feed adapter 7 present at the proximal end of the tube 5 and is evacuated at the distal end of the tube 5 in the direction of the arrows. An outer tube 8 is mounted around the tube 5 and is sealed at both ends and comprises evacuation holes 9 in its distal end zone and an evacuation adapter 10 at its proximal end. Thus, liquid can flow in the direction of the arrows from the bladder 1 through holes 9 and through the gap between outer tube 8 and tube 5 to evacuation adapter 10, where it will be drained. The instrument shown is a conventional urological continuous flow device.

An optics 11 sealed at 6 is placed inside the tube 5 and comprises an oblique-pointing objective 12 and a proximal ocular 13. Also a conductor 15 with insulation 14 passes through the tube 5 and supports at its distal end an exposed, active electrode 16 shown as a hook in the illustrative embodiment of the FIGURE. This active electrode 16 is connected by a conductor 17 to an hf generator 18.

So far, the described instrument corresponds to a conventional urological resection instrument with continuous flow allowing, for instance, prostate resection or, as shown in the FIGURE, allowing cutting tissue of the bladder wall by means of contact of the active electrode 16 with the bladder wall at 19, or coagulation may be carried out with it there.

As regards conventional instruments of the shown design, the required neutral electrode receiving the hf current passing from the active electrode through the body tissue would have to be placed far outside the shown body region, for instance on the surface of the thigh. Therefore the current would flow from the active electrode 16 through and deep into the body tissue. However, and in illustrative manner, the current in this process also might flow through the tissue toward the metal surfaces of the endoscope 4 and, at the ocular 13, it might jump toward the surgeon's eye. Furthermore, the current below the active electrode 16 might preferentially penetrate the tissue depth-wise and cause undesired burns also in tissue layers much below the bladder wall.

In order to preclude such drawbacks, the instrument shown in the FIGURE is fitted with a neutral electrode 20 in the form of a distal end of a wire 21 projecting from an insulating plastic sheath 22 and also placed inside the bladder, said sheath 22 also being sealed by the tube 5. The proximal end of wire 21 projects from the sheath 22 and is connected by a conductor 23 to hf generator 18.

As indicated by the dashed arrows of the FIGURE, because the liquid volume filling the bladder 1 is composed essentially of a poorly electrically conducting rinsing liquid supplied through the feed adapter 7, upon turning ON hf generator 18, current does not pass between active electrode 16 and neutral electrode 20. Instead, current only flows when contact is made between the active electrode 16 and the wall of bladder 1. The current then flows laterally (dashed arrows), being widely spread and of low current density over the entire surface of the bladder 1 to enter the liquid volume filling said bladder in order to pass through the liquid volume to neutral electrode 20. Accordingly, the desired high current density required for cutting or coagulation is achieved in the vicinity of active electrode 16. As regards the other surface zones where the current returns into the liquid, the current density is minute and no burns need be feared. The current density also drops very rapidly below the site 19 where the tissue makes contact with active electrode 16. The dreaded large depth of current penetration relating to conventional instruments is absent from the design shown.

As shown by the FIGURE, the treatment zone around the active electrode 16 is supplied constantly with electrolyte-lean and poorly conducting liquid. On one hand this feature assures that, in known manner, there will be good visibility from objective 12 to treatment zone 19 and, on the other hand, the current does not pass directly from active electrode 16 into the liquid but only along the detour through the tissue, as indicated by the dashed arrows.

The zone around neutral electrode 20 is advantageously kept at high conductivity by means of electrolyte-rich liquid. In the embodiment shown, the plastic tube 22 enclosing at its distal end wire 21 forming the neutral electrode 20 not only assumes an isolating function relative to the metal parts of the endoscope 4, but also is proximally connected through a pump 24 to a supply 25 of sodium salt solution fed by the pump through tube 22 to the zone around neutral electrode 20 as indicated there by the short arrows.

Inside the liquid volume filling bladder 1, permanent equilibrium is maintained by the instrument shown, and the zone around neutral electrode 20 is kept good-conducting using electrolyte-rich sodium salt solution at said equilibrium while the treatment zone around the active electrode 16 is kept poorly conductive by means of the inflow of electrolyte-lean liquid, and this state is maintained by constant liquid evacuation through evacuation holes 9 in outer tube 8.

However, good results also may be achieved if liquid volume 1 is uniformly enriched with electrolyte for instance using electrolyte-enriched rinsing liquid. However in that case and for applied hf current there is a constant bypass current, through liquid volume 1, between active electrode 16 and neutral electrode 20. But this current only loads hf generator 18, that is, its drawbacks are technical. The patient is not stressed by this bypass current because it does not pass through body tissue, only through liquid volume 1.

As shown by the FIGURE, neutral electrode 20 is surrounded by a contact guard 26 fitted with orifices to form a cage and mounted at the end of tube 22. Contact guard 26 encloses neutral electrode 20 while spaced from it. By means of orifices, contact guard 26 is in liquid communication with liquid volume 1. Contact guard 26 is made of an electrically insulating material.

If neutral electrode 20 were positioned other than in the idealized manner shown approximately centrally in the liquid volume 1, but instead during motions of the endoscope 4 were to undesirably touch the tissue surface, the current path would be closed directly through the tissue between the neutral and the active electrodes 20 and 16 resp. Both electrodes would act equally in cutting or coagulating manner, as in a bipolar instrument. However, because cutting with neutral electrode 20 is undesirable, contact guard 26 ensures that even in unwanted contact with the tissue, neutral electrode 20 always is kept a distance away and is prevented from exerting any cutting or coagulating action.

Instead of the embodiment shown in the FIGURE in which the contact-guard 26 shown as a cage, the neutral electrode 20 also may have a much simpler design wherein it does not project beyond the end of orthogonally cut tube 22, thereby being enclosed by the tube's distal end, then also serving as a contact-guard, and in that neutral electrode 20 is in conducting contact, preferably reinforced by feed of electrolyte, with the liquid volume 1, as far as the distal opening of the tube.

The instrument may be widely modified relative to the shown embodiment.

For example, active electrode 16 may assume a number of different shapes depending on application. Illustratively, it may be a small plate for coagulation purposes or a conventional cutting loop as commonly used in resection work. For graphical simplicity, devices ordinarily present on such instruments and used to displace the active electrode 16 to carry out reciprocating cutting motions while the endoscope 4 is stationary have been omitted from the FIGURE.

In the embodiment shown, neutral electrode 20 is a wire electrode which is advantageously fitted with devices (not shown) allowing it to be advanced and retracted into and from the shown work position.

Basically and in a variation from the embodiment shown, use may also be made of several tubes placed into the bladder 1, for instance one tube being introduced as shown through the urethra 3 and another tube being pierced through supra-pubically by means of a trocar. In such a design the feed of rinsing liquid may be implemented through the tube placed in the urethra and the evacuation of liquid may be implemented through the supra-pubically placed tube. In that case, neutral electrode 20 also may be put in place through the supra-pubic tube. However, the neutral electrode also may be put in place without a tube, for instance within a flexible catheter introduced in an appropriate manner into the cavity. Again, any feed of electrolyte-rich liquid to neutral electrode 20 may be implemented in a manner other than that shown, for instance using a separately emplaced tube terminating near neutral electrode 20.

Furthermore, in a simplified design of the shown endoscope 4, the neutral electrode may be made part of the endoscope in the vicinity of the distal end of tube 5 or of outer tube 8, for instance as a non-insulated metal ring always immersed in liquid volume 1. In this case, the outer zones of the tube 5 or outer tube 8 located proximally from the electrode ring must be insulated outwardly to prevent current from passing directly through the tissue, that is the wall of the urethra 3, to the neutral electrode. Illustratively, tube 5 as a whole may be designed to be the neutral electrode, whereas the outer tube 8 is made of plastic and assures the required insulation.

As already mentioned, it is important for proper functioning of the neutral electrode that it be in liquid contact only with liquid volume 1. Current from the neutral electrode should only pass through liquid volume 1 through body tissue. If the neutral electrode were to make direct contact with the body tissue, current at the contact site would be of high density, as in the case of the active electrode 16, flowing into the body tissue and would entail unwanted burns. In the embodiment shown, contact guard 26 precludes contact between neutral electrode 20 and the body tissue. However, other ways may also be used to prevent direct contact between the neutral electrode and the body tissue.

Illustratively, the hf current may be monitored using electrical test equipment, so that, in case of increased current caused by contact between body tissue and the neutral electrode 20, the current shall be cut. Moreover, other electrical test equipment may be used such as are described in European patent document 0,390,937 A1. For instance, two tightly adjacent neutral electrodes connected to the hf generator may be used, the electrical resistance between them being ascertained by a measuring system. This resistance between the two neutral electrodes varies strongly when these neutral electrodes make contact with tissue. Such an event can be determined by this measuring system and be used to shut off the current.

Such a design is especially advantageous when the neutral electrode in the already discussed embodiment is mounted at the distal end of tube 5 or especially at the distal end of outer tube 8. As shown by the FIGURE, in that case the neutral electrode is very close to the body tissue and may frequently make contact with the tissue when the shown instrument is being displaced. In such a case the electrical measuring system assures shutting off the hf generator 18 and as a result tissue injuries are avoided. Such a neutral electrode may consist of two parts electrically separately connected to the hf generator 18, for instance being in the form of adjacent narrow electrode strips mounted on the surface of outer tube 8 immediately next to its distal end.

I claim:

1. An endoscopic instrument for high-frequency surgery on tissue in a body cavity containing an electrically conductive fluid, the instrument comprising the combination of a high-frequency generator for producing high-frequency electrical energy for surgical use;

a first, active electrode connected to said generator, said first electrode being adapted to be inserted into a body cavity for surgical contact with tissue;

a second, neutral electrode connected to said generator and being adapted to be inserted into the body cavity; and an electrically non-conductive housing enclosing said second electrode and having at least one opening therethrough to permit flow of conductive liquid into said housing, said housing being adapted to prevent direct contact of said second electrode with body tissue.

2. An instrument according to claim 1 further comprising a tube, said first and second electrodes being insertable through said tube.

3. An instrument according to claim 1 further including a rinsing system adapted to flow electrically conductive rinsing liquid into the cavity.

4. An instrument according to claim 3 and including an evacuation system adapted to remove rinsing liquid from the cavity.

* * * * *